(12) United States Patent
Mujwid et al.

(10) Patent No.: US 12,070,390 B2
(45) Date of Patent: Aug. 27, 2024

(54) PUMP ASSEMBLY WITH PRESSURE RELIEF MECHANISM FOR A PENILE PROSTHESIS

(71) Applicant: Boston Scientific Scimed, Inc., Maple Grove, MN (US)

(72) Inventors: James Ryan Mujwid, Hudson, WI (US); Mark Edward DiLoreto, Chaska, MN (US); Nicholas Washuta, Orono, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 732 days.

(21) Appl. No.: 17/247,340

(22) Filed: Dec. 8, 2020

(65) Prior Publication Data
US 2021/0228359 A1 Jul. 29, 2021

Related U.S. Application Data

(60) Provisional application No. 62/967,317, filed on Jan. 29, 2020.

(51) Int. Cl.
*A61F 2/26* (2006.01)

(52) U.S. Cl.
CPC ........ *A61F 2/26* (2013.01); *A61F 2230/0023* (2013.01); *A61F 2250/0013* (2013.01)

(58) Field of Classification Search
CPC ....................................................... A61F 2/26
USPC ........................................................... 600/40
See application file for complete search history.

(56) References Cited

U.S. PATENT DOCUMENTS

| 4,364,379 | A | * | 12/1982 | Finney | A61F 2/26 |
| | | | | | 600/40 |
| 4,898,158 | A | * | 2/1990 | Daly | A61F 2/26 |
| | | | | | 600/40 |
| 7,914,439 | B2 | | 3/2011 | Kuyava et al. | |
| 2006/0135845 | A1 | * | 6/2006 | Kuyava | A61F 2/26 |
| | | | | | 600/40 |

(Continued)

FOREIGN PATENT DOCUMENTS

WO 2021026558 A1 2/2021

OTHER PUBLICATIONS

International Search Report and Written Opinion for PCT Application No. PCT/US2020/070889, mailed on Mar. 19, 2021, 12 pages.

(Continued)

*Primary Examiner* — Samuel G Gilbert
(74) *Attorney, Agent, or Firm* — Brake Hughes Bellermann LLP

(57) ABSTRACT

According to an aspect, an inflatable penile prosthesis includes a fluid reservoir configured to hold fluid, an inflatable member, and a pump assembly configured to transfer the fluid between the fluid reservoir and the inflatable member, the pump assembly including a pump bulb, a valve body, a valve disposed within the valve body, a first fluid port configured to be fluidly coupled to the fluid reservoir, and a second fluid port configured to be fluidly coupled to the inflatable member, the valve being configured to move between an inflation position and a deflation position, wherein the valve body includes a sealing surface configured to engage the valve to form seal, the valve body includes a slot disposed adjacent the sealing surface.

20 Claims, 13 Drawing Sheets

(56) References Cited

U.S. PATENT DOCUMENTS

2007/0142700 A1 6/2007 Fogarty et al.
2019/0307567 A1 10/2019 Mujwid et al.

OTHER PUBLICATIONS

Second Examination Report for Australian Application No. 2020426682, mailed Nov. 30, 2023, 4 pages.

\* cited by examiner

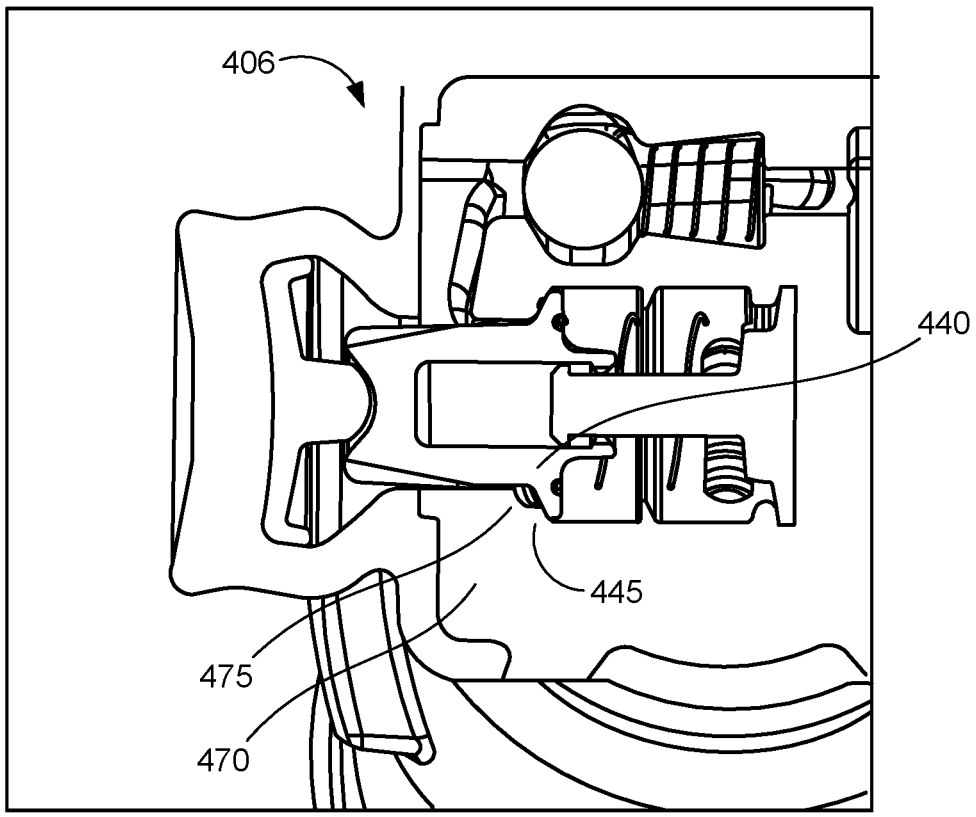
FIG. 8
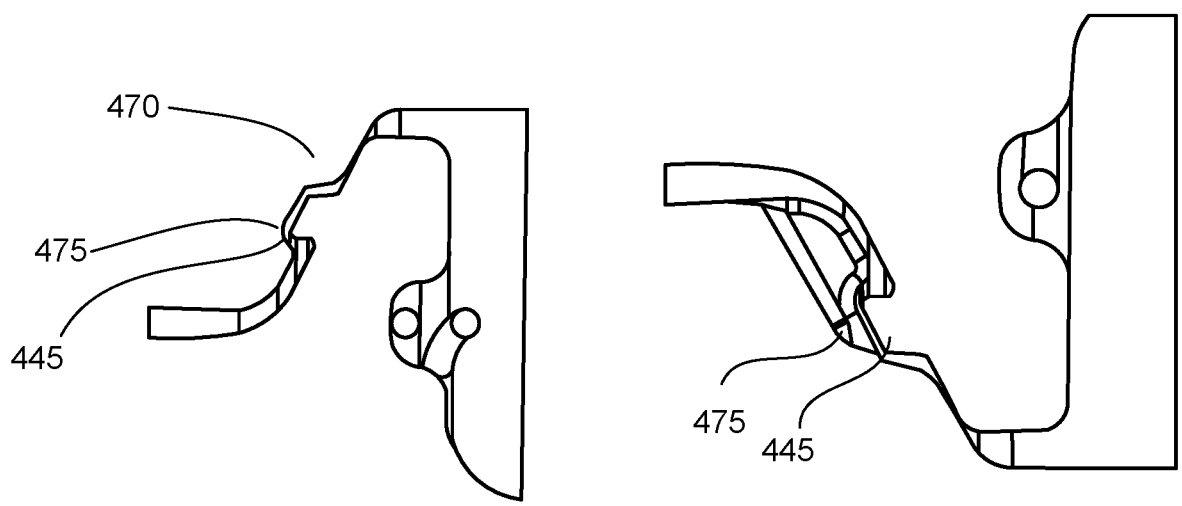
FIG. 9
FIG. 10

PUMP ASSEMBLY WITH PRESSURE RELIEF MECHANISM FOR A PENILE PROSTHESIS

CROSS-REFERENCE TO RELATED APPLICATION

This application claims priority to U.S. Provisional Patent Application No. 62/967,317, filed on Jan. 29, 2020, entitled "PUMP ASSEMBLY WITH PRESSURE RELIEF MECHANISM FOR A PENILE PROSTHESIS", the disclosure of which is incorporated by reference herein in its entirety.

TECHNICAL FIELD

This disclosure relates generally to bodily implants and more specifically to bodily implants, such as a penile prosthesis that includes a pump.

BACKGROUND

One treatment for male erectile dysfunction is the implantation of a penile prosthesis that mechanically erects the penis. Some existing penile prostheses include inflatable cylinders or members that can be inflated or deflated using a pump mechanism. The pump mechanism pulls fluid from a fluid reservoir and then transfers the fluid to the inflatable members. The pump mechanism may include a pump bulb and a valve body that includes one or more valve components. According to some existing designs of inflatable penile prostheses, the valve components may be exposed to a large amount of pressure and cause the pump to malfunction.

SUMMARY

According to an aspect, an inflatable penile prosthesis includes a fluid reservoir configured to hold fluid, an inflatable member, and a pump assembly configured to transfer the fluid between the fluid reservoir and the inflatable member, the pump assembly including a pump bulb, a valve body, a valve disposed within the valve body, a first fluid port configured to be fluidly coupled to the fluid reservoir, and a second fluid port configured to be fluidly coupled to the inflatable member, the valve being configured to move between an inflation position and a deflation position, wherein the valve body includes a sealing surface configured to engage the valve to form seal, the valve body includes a slot disposed adjacent the sealing surface.

In some embodiments, the sealing surface is disposed between the slot and the valve. In some embodiments, the slot is a first slot, the valve body includes a second slot. In some embodiments, the slot is a first slot, the valve body includes a second slot disposed adjacent the sealing surface, the sealing surface being disposed between the second slot and the valve.

In some embodiments, the valve includes an elongate portion and an engagement portion, the engagement portion having a surface configured to engage the sealing surface of the valve body.

In some embodiments, the slot is triangular shaped. In some embodiments, the slot includes a linear portion.

In some embodiments, the pump assembly includes a biasing member, the biasing member being configured to bias the valve towards the sealing surface. In some embodiments, the pump assembly includes a biasing member, the biasing member being configured to engage the valve and bias the valve towards the sealing surface. In some embodiments, the pump assembly includes a spring member.

In some embodiments, the valve includes a surface configured to engage the sealing surface, the surface of the valve including a projection portion. In some embodiments, the valve includes a projection portion, the projection portion being configured to engage the sealing surface of the valve body. In some embodiments, the valve includes a first member and a second member, the first member being configured to move with respect to the second member. In some embodiments, the valve body includes a projection, the valve defines a cavity, the valve cavity being configured to receive at least a portion of the projection of the valve body. In some embodiments, the valve defines a groove configured to receive at least a portion of a biasing member.

In another implementation, an inflatable penile prosthesis includes a fluid reservoir configured to hold fluid; an inflatable member; a pump assembly configured to transfer the fluid between the fluid reservoir and the inflatable member, the pump assembly including a pump bulb, a valve body, a valve disposed within the valve body, a first fluid port configured to be fluidly coupled to the fluid reservoir, and a second fluid port configured to be fluidly coupled to the inflatable member, the valve being configured to move between an inflation position and a deflation position; and a pressure relief valve, wherein the valve defines a cavity, the pressure relieve valve is disposed within the cavity and is configured to move within the cavity.

In some embodiments, the valve defines a groove configured to receive a biasing member. In some embodiments, the valve defines a groove configured to receive a portion of a spring.

In another implementation, an inflatable penile prosthesis includes a fluid reservoir configured to hold fluid; an inflatable member; and a pump assembly configured to transfer the fluid between the fluid reservoir and the inflatable member, the pump assembly including a pump bulb, a valve body, a valve disposed within the valve body, a first fluid port configured to be fluidly coupled to the fluid reservoir, and a second fluid port configured to be fluidly coupled to the inflatable member, the valve being configured to move between an inflation position and a deflation position, wherein the valve body includes a sealing surface configured to engage the valve to form seal, the valve body includes a first slot disposed adjacent the sealing surface, the valve body includes a second slot disposed adjacent the sealing surface, the sealing surface being disposed between the first slot and the valve, the sealing surface being dispose between the second slot and the valve.

In some embodiments, the pump assembly includes a biasing member, the biasing member being configured to bias the valve towards the sealing surface.

BRIEF DESCRIPTION OF THE DRAWINGS

FIGS. 8-11 illustrate portions of a penile prosthesis according to an aspect.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure.

Figure 1:
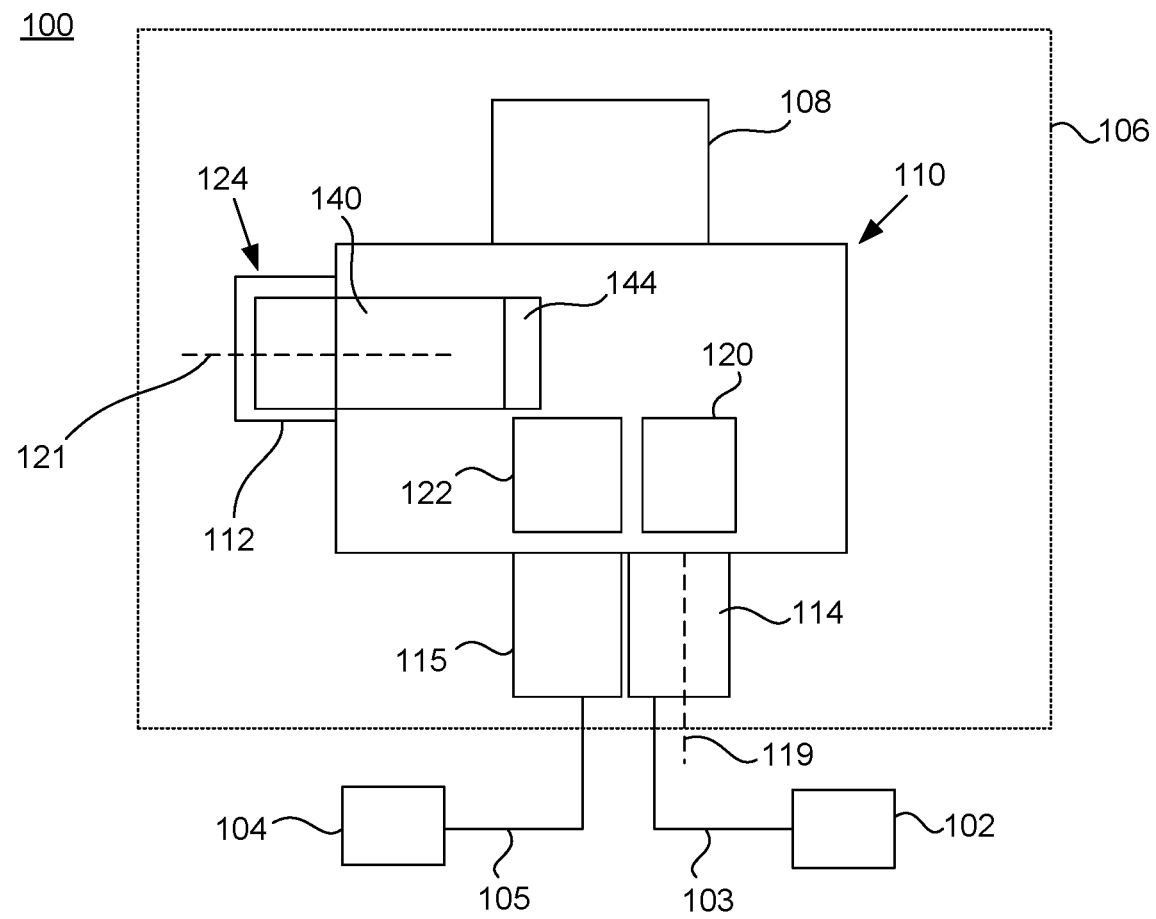
FIG. 1 schematically illustrates an inflatable penile prosthesis according to an aspect.

FIG. 1 illustrates an inflatable penile prosthesis 100 including a fluid reservoir 102, an inflatable member 104, and a pump assembly 106 configured to transfer fluid between the fluid reservoir 102 and the inflatable member 104 according to an aspect. The inflatable member 104 may be implanted into the corpus cavernosae of the user, the fluid reservoir 102 may be implanted in the abdomen or pelvic cavity of the user (e.g., the fluid reservoir 102 may be implanted in the lower portion of the user's abdominal cavity or the upper portion of the user's pelvic cavity), and the pump assembly 106 may be implanted in the scrotum of the user.

The pump assembly 106 includes a pump bulb 108, a valve body 110, a push valve 124 movably coupled to the valve body 110, a first fluid port 114 fluidly coupled to the fluid reservoir 102 (via a first conduit connector 103), and a second fluid port 115 fluidly coupled to the inflatable member 104 (via a second conduit connector 105). The first fluid port 114 and the second fluid port 115 may extend from an end portion of the valve body 110. In some examples, the fluid transfer ports are disposed on (or defined by) a tube adaptor (e.g., a triple tube adaptor) that is separate from the valve body 110, and the tube adaptor is coupled to the valve body 110. In some examples, the first fluid port 114 includes an elongated tubular member defining a cavity. In some examples, the second fluid port 115 includes two separate elongated tubular members (e.g., one tubular member being fluidly coupled to a first cylinder member of the inflatable member 104 and another tubular member being fluidly coupled to a second cylinder member of the inflatable member 104).

The push valve 124 is configured to move from an inflation position to a deflation position along an axis 121 within a bore of the valve body 110 when pressed by a user in order to control the direction of the fluid through the fluid passageways of the valve body 110. The push valve 124 includes a movable valve element 140 and a biasing member 144 that biases the movable valve element 140 to the inflation position. In some examples, the movable valve element 140 is configured to move to the deflation position in a linear direction based on a single instantaneous push of the movable valve element 140 by a user. The pump assembly 106 includes a button component 112 that encloses a portion of the movable valve element 140 when the movable valve element 140 is in the inflation position. The button component 112 may be a flexible button-shaped material that extends over the movable valve element 140.

In some examples, the movable valve element 140 includes a directional control valve. In some examples, the movable valve element 140 includes one or more ring members (e.g., annular rings or retainer rings). In some examples, the biasing member 144 includes a spring.

The design of the push valve 124 may reduce (or eliminate) the possibility for the pump bulb 108 to get stuck in a collapsed state even if the first squeeze to switch from the deflation mode to the inflation mode does not successfully move the movable valve element 140 to the inflation position. When the movable valve element 140 is in the inflation position, the inflatable penile prosthesis 100 is in an inflation mode (or inflation cycle). When the movable valve element 140 is in the deflation position, the inflatable penile prosthesis 100 is in a deflation mode (or deflation cycle). In some examples, a single, instantaneous push of the movable valve element 140 transfers the inflatable penile prosthesis 100 to the deflation position (e.g., as opposed to pressing and holding the movable valve element 140 for a certain predetermined time). In some examples, movement of the movable valve element 140 to the deflation position causes a fluid pathway to open between the second fluid port 115 and the first fluid port 114 such that fluid can be transferred from the inflatable member 104 to the fluid reservoir 102 via the pump assembly 106 in a manner that bypasses the pump bulb 108.

In contrast, in the inflation mode, the pump bulb 108 is used to transfer fluid from the fluid reservoir 102 to the inflatable member 104. For example, the user may depress (or squeeze) the pump bulb 108 and then release the pump bulb 108, and then repeat these operations until the desired rigidity is achieved in the inflatable member 104. The release of the pump bulb 108 creates a suction force that pulls fluid from the fluid reservoir 102 to the pump bulb 108, and the depression of the pump bulb 108 expels the fluid from the pump bulb 108 to the inflatable member 104. In some examples, in the inflation mode, the valve body 110 provides an optimized fluid passageway via the push valve 124 that may decrease the pressure drop across the push valve 124 for faster inflate time and/or decrease the fluid resistance thereby requiring less pump bulb squeeze force to inflate.

In some embodiments, the valve assembly 106 includes a pressure relief mechanism. For example, in some embodiments, the valve assembly 106 includes a pressure relief mechanism that is configured to relieve pressure on the valve member or movable valve element 140 during the inflate mode if the pressure on the valve member or movable valve element 140 becomes too great. In some embodiments, the pressure relief mechanism helps prevent the valve member or movable valve element 140 from becoming dislodged from its appropriate location within the pump assembly 106 or from otherwise becoming nonfunctional.

In some embodiments, the pressure relief mechanism includes slots or grooves defined by the valve body 110. In some embodiments, the pressure relief mechanism includes grooves or slots defined by the valve member 140. In other embodiments, the pressure relief mechanism includes a valve member 140 that has a secondary valve or secondary valve or secondary valve member.

The pump bulb 108 may be a flexible member defining a cavity. The pump bulb 108 is coupled to and extends from the valve body 110. In some examples, the pump bulb 108 extends from the valve body 110 in a direction that is opposite to the direction in which the first fluid port 114 and the second fluid port 115 extend from the valve body 110 (e.g., located on opposite ends of the valve body 110). The pump bulb 108 may be a squeeze pump. In some examples, the pump bulb 108 includes ribbing or dimples to aid the user in gripping the pump bulb 108. As indicated above, the pump bulb 108 may use suction and pressure to move the fluid in and out of the cavity of the pump bulb 108 in the inflation mode. For example, the user may depress or squeeze the pump bulb 108 to expel the fluid out of the cavity, and, when the flexible member returns to its original shape, the resulting suction pushes the fluid into the cavity of the pump bulb 108. In some examples, the pump bulb 108 may have a bulb spring rate that is designed to refill the pump bulb 108 in a selected time frame.

The valve body 110 defines one or more fluid passageways through the valve body 110. The valve body 110 includes valve components disposed within the fluid passageways to control the flow of the fluid through the valve body 110 in the inflation mode and the deflation mode. In some examples, the valve body 110 includes a block of material that defines the fluid passageways and encloses the valve components. In some examples, the valve body 110 includes a silicone material. In some examples, the valve body 110 may be molded from a silicone material having a medium durometer value. In some examples, the pump assembly 106 includes an outer protective casing that is disposed over the valve body 110. In some examples, the outer protective casing has a material (e.g., a polymer material) that is different from the valve body 110. In some examples, the outer protective casing includes one or more tactile features that help the user locate the valve body 110 (in order to locate the push valve 124). In some examples, the tactile features include protruded portions, ridges, grooves, bumps, and/or depressions.

The valve body 110 includes a refill valve 120 and an inflation valve 122. In some examples, the valve body 110 includes an anti-auto inflate valve. The refill valve 120 may be used when the pump bulb 108 is refilled. The refill valve 120 is not used in the deflation mode. In some examples, the refill valve 120 is a one-way valve. In some examples, the refill valve 120 is disposed in a fluid passageway within the valve body 110 between the first fluid port 114 and the pump bulb 108. In some examples, the fluid passageway having the refill valve 120 that extends between the first fluid port 114 and the pump bulb 108 is used only for refilling the pump bulb 108 (e.g., a separated fluid pathway), which may decrease bulb refill time (e.g., deceases the wait time between squeezes). In some examples, the refill valve 120 is fluidly coupled to the bore (where the push valve 124 moves within) and the pump bulb 108.

In some examples, the refill valve 120 is aligned with the first fluid port 114. For example, the refill valve 120 may have an inlet and an outlet, where fluid enters the inlet from the first fluid port 114 and exits the outlet to the pump bulb 108. The first fluid port 114 may define a longitudinal axis 119 that extends along the fluid pathway (e.g., between the inlet and the outlet) of the refill valve 120. In some examples, the longitudinal axis 119 is orthogonal to the axis 121. The alignment of the refill valve 120 with the first fluid port 114 may minimize fluid pathway tortuosity, and/or decrease pressure drop across the refill valve 120. In some examples, the refill valve 120 includes a floating check ball with fluting (which may increase or maximize fluid velocity across the refill valve 120). In some examples, the refill valve 120 includes a biasing member that biases the refill valve 120 to a sealing position. In some examples, the biasing member includes a spring. In some examples, the refill valve 120 does not include a biasing member.

The inflation valve 122 may be disposed within a fluid passageway between the pump bulb 108 and the push valve 124. The inflation valve 122 may be used during the inflation of the inflatable member 104 (e.g., when the fluid is transferred from the pump bulb 108 to the inflatable member 104). The inflation valve 122 is not used during the deflation mode. In some examples, the inflation valve 122 is a one-way valve. In some examples, the inflation valve 122 includes a check ball and a biasing member. The biasing member may bias the check ball to a sealing position. In some examples, the biasing member includes a spring.

In the inflation position (and when the user is operating the pump bulb 108), the fluid may flow from the first fluid port 114 (from the fluid reservoir 102) to the pump bulb 108 via the refill valve 120, and from the pump bulb 108 to the second fluid port 115 via the inflation valve 122 and the push valve 124 (and then to the inflatable member 104). In response to the movable valve element 140 being pressed to the deflation position, the position in the movable valve element 140 within the bore of the valve body 110 may open a fluid passageway in the valve body 110 to transfer fluid from the inflatable member 104 to the fluid reservoir 102 that bypasses the pump bulb 108. For example, the movable valve element 140, when moved to the deflation position, is configured to change the fluid passageway through the bore to transfer fluid from the second fluid port 115 to the first fluid port 114 such that the pump bulb 108 is bypassed. In some examples, due to the pressure inside of the inflatable member 104, some of the fluid may be automatically transferred from the inflation member 104 to the fluid reservoir 102 via the pump assembly 106, and then the user may squeeze the inflatable member 104 to transfer some of the remaining fluid in the inflatable member 104.

Each of the first conduit connector 103 and the second conduit connector 105 may define a lumen configured to transfer the fluid to and from the pump assembly 106. The first conduit connector 103 may be coupled to the pump assembly 106 and the fluid reservoir 102 such that fluid can be transferred between the pump assembly 106 and the fluid reservoir 102 via the first conduit connector 103. For example, the first conduit connector 103 may define a first lumen configured to transfer fluid between the pump assembly 106 and the fluid reservoir 102. The first conduit connector 103 may include a single or multiple tube members for transferring the fluid between the pump assembly 106 and the fluid reservoir 102.

The second conduit connector 105 may be coupled to the pump assembly 106 and the inflatable member 104 such that fluid can be transferred between the pump assembly 106 and the inflatable member 104 via the second conduit connector 105. For example, the second conduit connector 105 may define a second lumen configured to transfer fluid between the pump assembly 106 and the inflatable member 104. The second conduit connector 105 may include a single or multiple tube members for transferring the fluid between the pump assembly 106 and the inflatable member 104. In some examples, the first conduit connector 103 and the second conduit connector 105 may include a silicone rubber material. In some examples, the pump assembly 106 may be directly connected to the fluid reservoir 102.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of inflatable cylinders or at least two cylinders, e.g., a first cylinder member and a second cylinder member. The volumetric capacity of the inflatable member 104 may depend on the size of the inflatable cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

The fluid reservoir 102 may include a container having an internal chamber configured to hold or house fluid that is used to inflate the inflatable member 104. The volumetric capacity of the fluid reservoir 102 may vary depending on the size of the inflatable penile prosthesis 100. In some examples, the volumetric capacity of the fluid reservoir 102 may be 3 to 150 cubic centimeters. In some examples, the fluid reservoir 102 is constructed from the same material as the inflatable member 104. In other examples, the fluid reservoir 102 is constructed from a different material than the inflatable member 104. In some examples, the fluid reservoir 102 contains a larger volume of fluid than the inflatable member 104.

Figure 2:
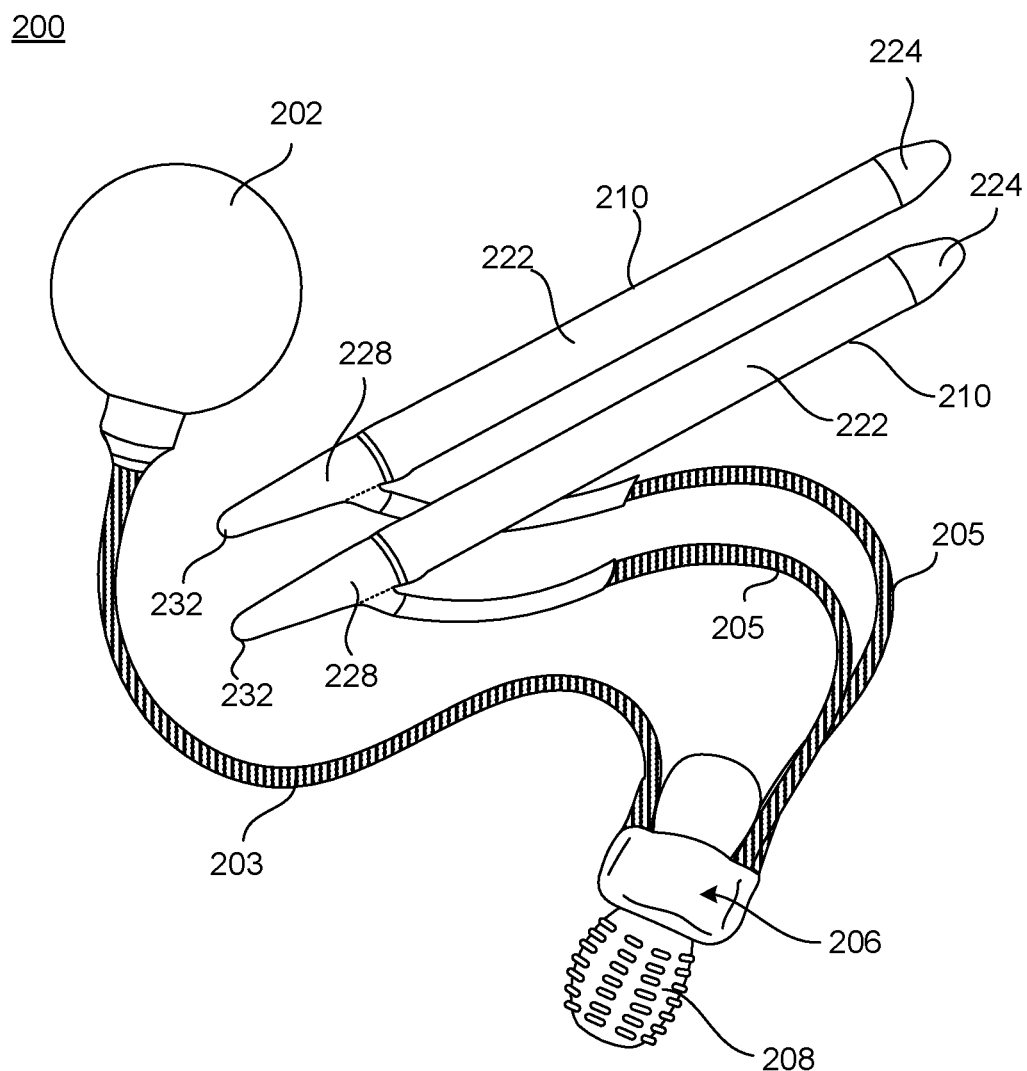
FIG. 2 illustrates an inflatable penile prosthesis according to an aspect.

FIG. 2 illustrates an inflatable penile prosthesis 200 having a pump assembly 206 according to an aspect. The pump assembly 206 may include any of the features of the pump assemblies (including the push valve) described with reference to the previous figures. The penile prosthesis 200 may include a pair of inflatable cylinders 210, and the inflatable cylinders 210 are configured to be implanted in a penis. For example, one of the inflatable cylinders 210 may be disposed on one side of the penis, and the other inflatable cylinder 210 may be disposed on the other side of the penis. Each inflatable cylinder 210 may include a first end portion 224, a cavity or inflation chamber 222, and a second end portion 228 having a rear tip 232.

The pump assembly 206 may be implanted into the patient's scrotum. A pair of conduit connectors 205 may attach the pump assembly 206 to the inflatable cylinders 210 such that the pump assembly 206 is in fluid communication with the inflatable cylinders 210. Also, the pump assembly 206 may be in fluid communication with a fluid reservoir 202 via a conduit connector 203. The fluid reservoir 202 may be implanted into the user's abdomen. The inflation chamber or portion 222 of the inflatable cylinder 210 may be disposed within the penis. The first end portion 224 of the inflatable cylinder 210 may be at least partially disposed within the crown portion of the penis. The second end portion 228 may be implanted into the patient's pubic region PR with the rear tip 232 proximate the pubic bone PB.

In order to implant the inflatable cylinders 210, the surgeon first prepares the patient. The surgeon often makes an incision in the penoscrotal region, e.g., where the base of the penis meets with the top of the scrotum. From the penoscrotal incision, the surgeon may dilate the patient's corpus cavernosae to prepare the patient to receive the inflatable cylinders 210. The corpus cavernosum is one of two parallel columns of erectile tissue forming the dorsal part of the body of the penis, e.g., two slender columns that extend substantially the length of the penis. The surgeon will also dilate two regions of the pubic area to prepare the patient to receive the second end portion 228. The surgeon may measure the length of the corpora cavernosae from the incision and the dilated region of the pubic area to determine an appropriate size of the inflatable cylinders 210 to implant.

After the patient is prepared, the penile prosthesis 200 is implanted into the patient. The tip of the first end portion 824 of each inflatable cylinder 210 may be attached to a suture. The other end of the suture may be attached to a needle member (e.g., Keith needle). The needle member is inserted into the incision and into the dilated corpus cavernosum. The needle member is then forced through the crown of the penis. The surgeon tugs on the suture to pull the inflatable cylinder 210 into the corpus cavernosum. This is done for each inflatable cylinder 210 of the pair. Once the inflation chamber 222 is in place, the surgeon may remove the suture from the tip. The surgeon then inserts the second end portion 228. The surgeon inserts the rear end of the inflatable cylinder 210 into the incision and forces the second end portion 228 toward the pubic bone PB until each inflatable cylinder 210 is in place.

A pump bulb 208 of the pump assembly 206 may be squeezed or depressed by the user in order to facilitate the transfer of fluid from the fluid reservoir 202 to the inflatable cylinders 210. For example, in the inflation mode, while the user is operating the pump bulb 208, the pump bulb 208 may receive the fluid from the fluid reservoir 802, and then output the fluid to the inflatable cylinders 210. When the user switches to the deflation mode, at least some of the fluid can automatically be transferred back to the fluid reservoir 202 (due to the difference in pressure from the inflatable cylinders 210 to the fluid reservoir 202). Then, the user may squeeze the inflatable cylinders 210 to facilitate the further transfer of fluid through the pump bulb 208 to the fluid reservoir 202.

Figure 3:
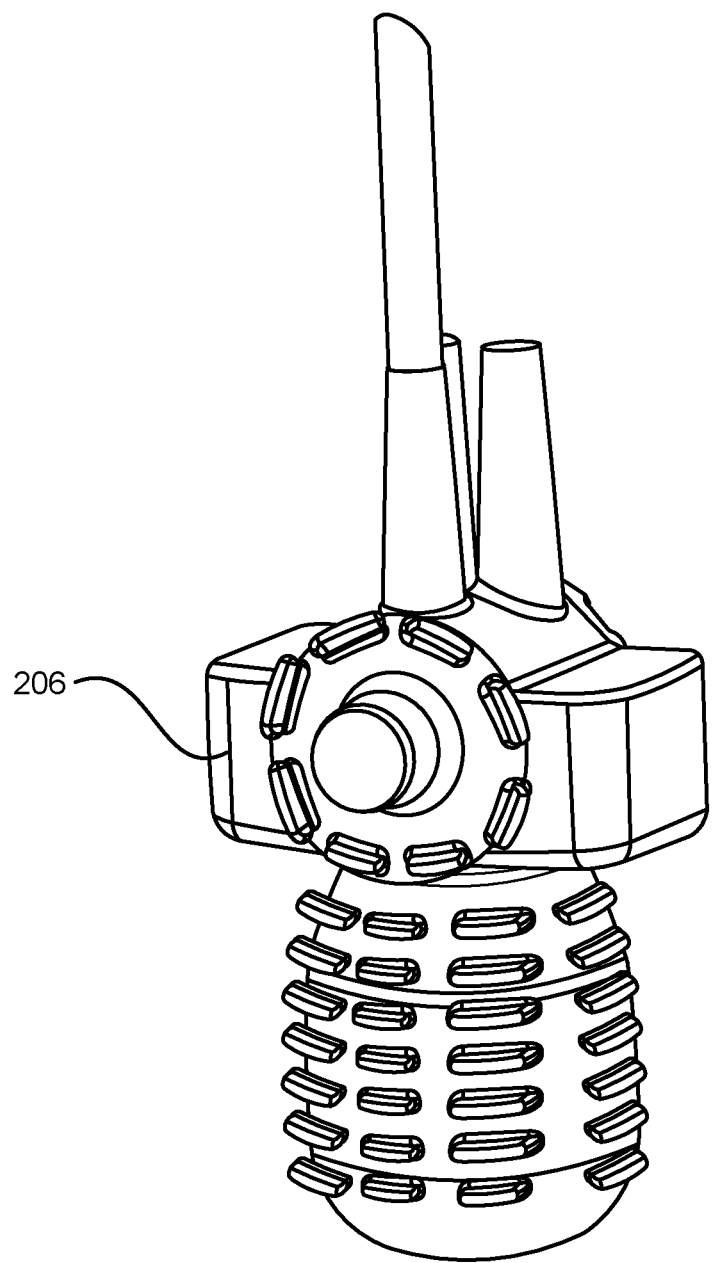
FIG. 3 is a perspective view of a portion of the penile prosthesis of FIG. 2.
Figure 4:
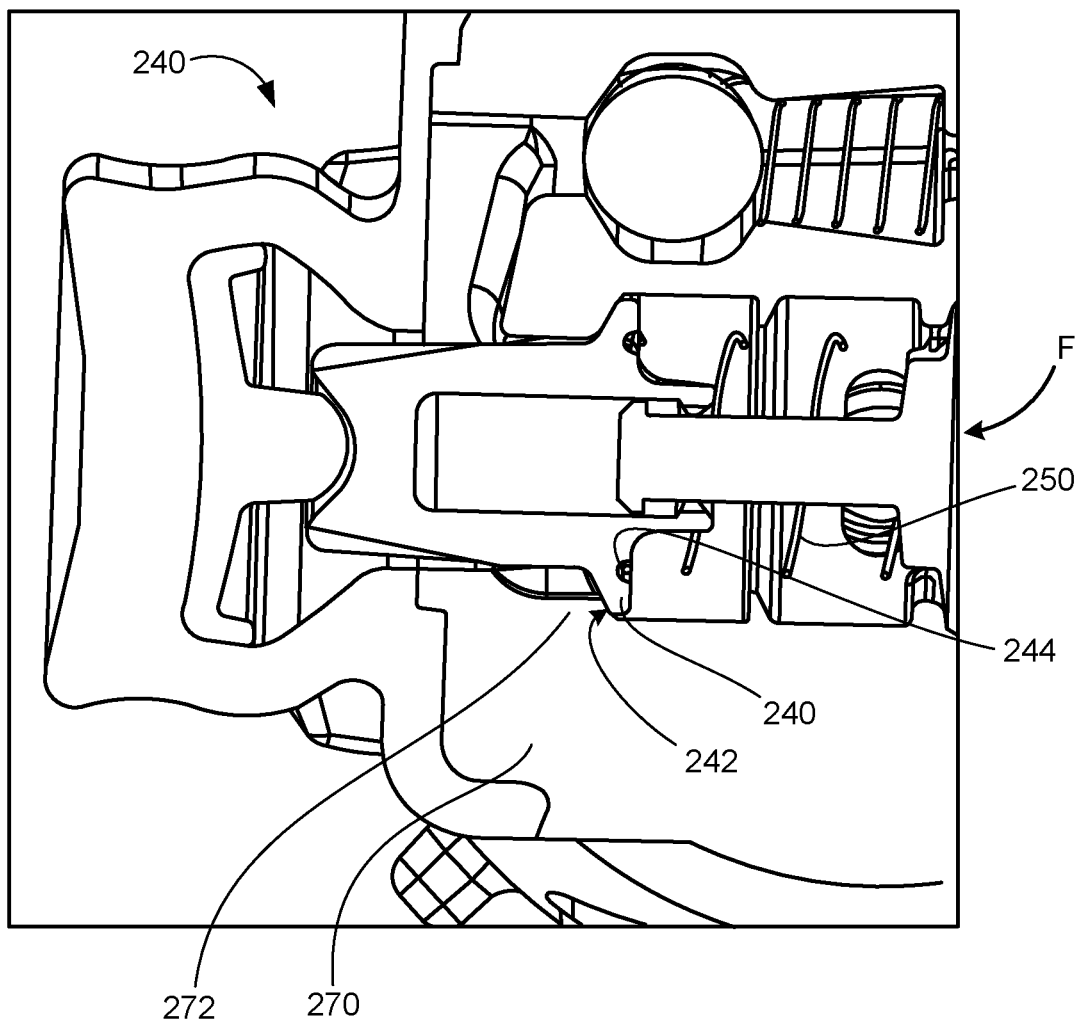
FIGS. 4-5 are cross-sectional views of a portion of the penile prosthesis of FIG. 2.
Figure 5:
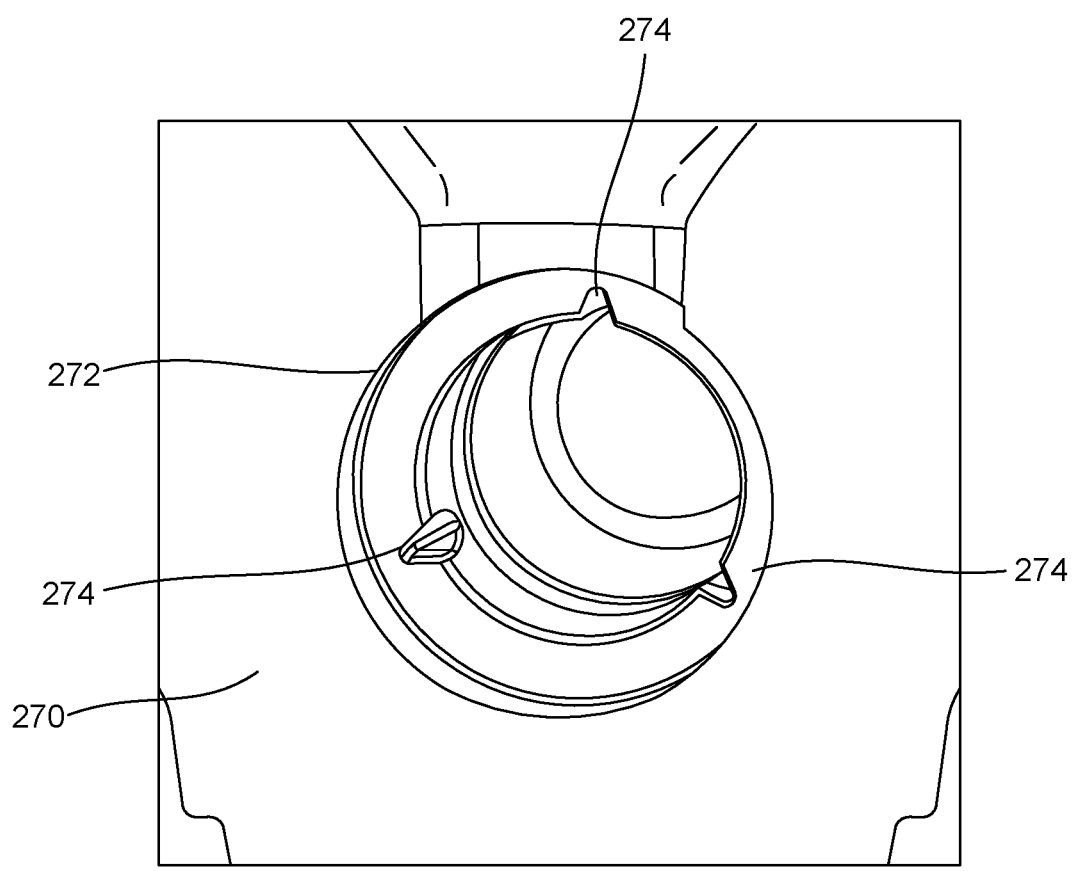

FIGS. 3-5 illustrate the pump assembly 206. The movable valve element 240 is disposed within the valve body 270 and is configured to move within the valve body 270.

The valve assembly 206 includes a pressure relief mechanism. For example, the valve assembly 206 includes a pressure relief mechanism that is configured to relieve pressure on the valve member or movable valve element 240 during the inflate mode if the pressure on the valve member or movable valve element 240 becomes too great. In some embodiments, the pressure relief mechanism helps prevent the valve member or movable valve element 240 from becoming dislodged from its appropriate location within the pump assembly 206 or from otherwise becoming nonfunctional.

In the illustrated embodiment, valve body 270 includes or defines a sealing surface 272. The sealing surface 272 is configured to contact or engage the movable valve element 240 to form a fluidic seal. For example, in some embodiments, the movable valve element 240 is configured to contact or engage the sealing surface 272 when the movable valve element 240 is in the inflate position (and when the pump assembly 206 is in the inflate mode).

In the illustrated embodiment, the valve body 270 includes or defines slots, grooves, or passageways 274. In the illustrated embodiment, the valve body 270 includes three slots, grooves, or passageways 274. In other embodiments, the valve body 270 includes a different number of slots. For example, in some embodiments, the valve body 270 includes a single slot or groove. In other embodiments, the valve body includes more than one slot or groove. In the illustrated embodiment, the valve body includes or defines triangular shaped slots or grooves. In other embodiments, the slots or grooves are of a different shape.

In the illustrated embodiment, the sealing surface 272 is located or disposed between the slots 274 and the movable valve element 240. In some embodiments, if the movable valve element 240 is exposed to an excessive amount of pressure it will tend to be forced in the direction of arrow F. In the illustrated embodiment, as this happens the movable valve element 240 will move past the sealing surface and the pressure may be relieved via the slots 274. Specifically, the fluid that is adjacent the movable valve element 240 may pass the movable valve element 240 via the slots 274 thereby relieving the pressure. In some embodiments, the pressure reduction helps prevent the movable valve element 240 from becoming forced into an incorrect position within the valve body 270 or otherwise cause the movable valve element 240 from malfunctioning.

In the illustrated embodiment, the movable valve element 240 includes a surface 242 that is configured to engage the sealing surface 272 of the valve body 270. Additionally, the movable valve element 240 includes or defines a groove 244 that is configured to receive or engage a biasing member 250. In the illustrated embodiment, the biasing member 250 is a spring member and is configured to bias the movable valve element 240 towards the sealing surface 272 of the valve body 270.

Figure 6:
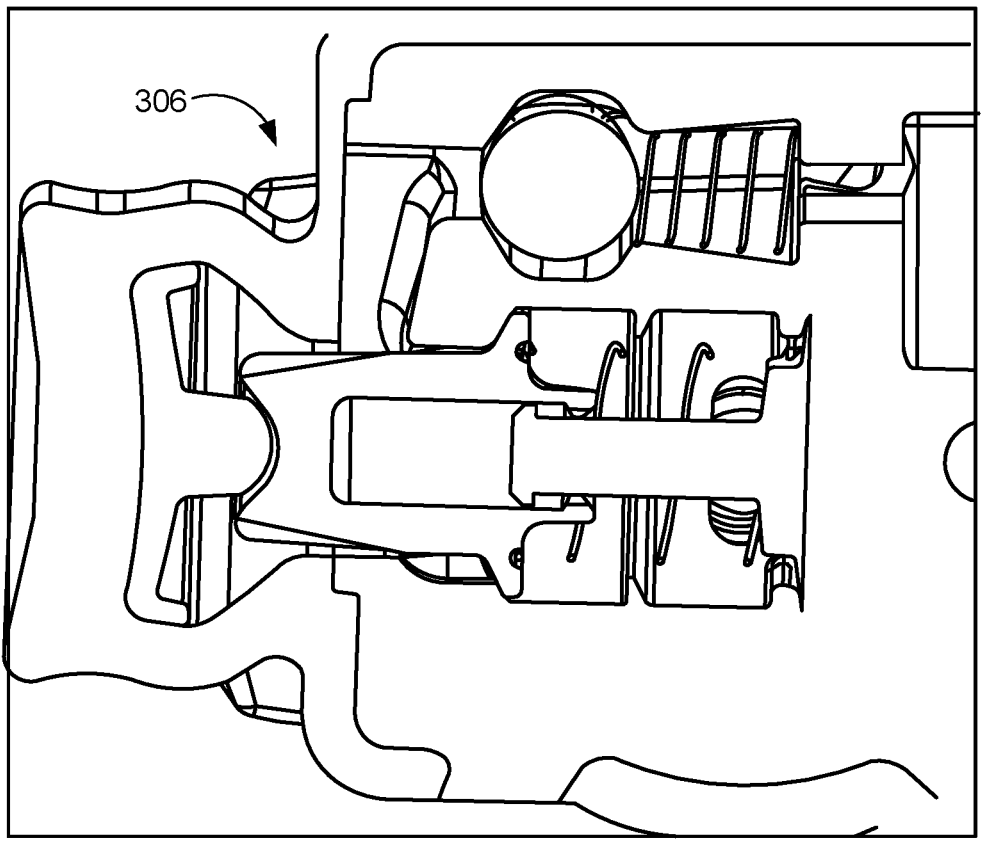
FIGS. 6-7 are cross-sectional views of a portion of a penile prosthesis according to an aspect.
Figure 7:
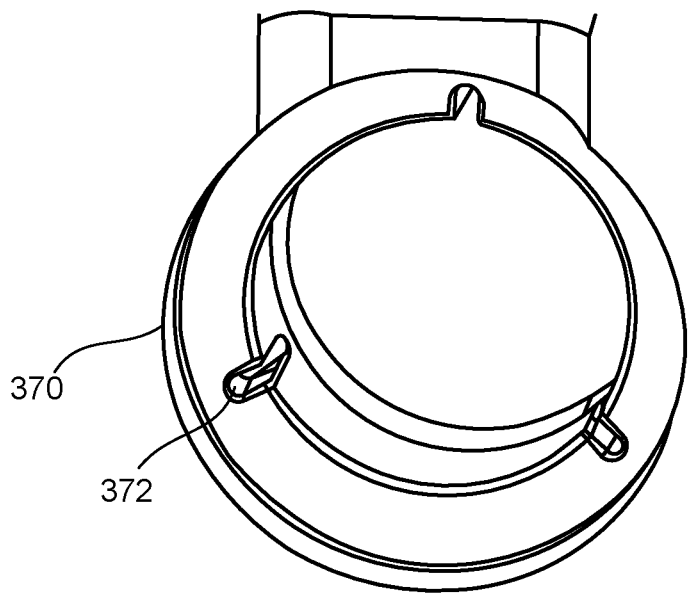
Figure 11:
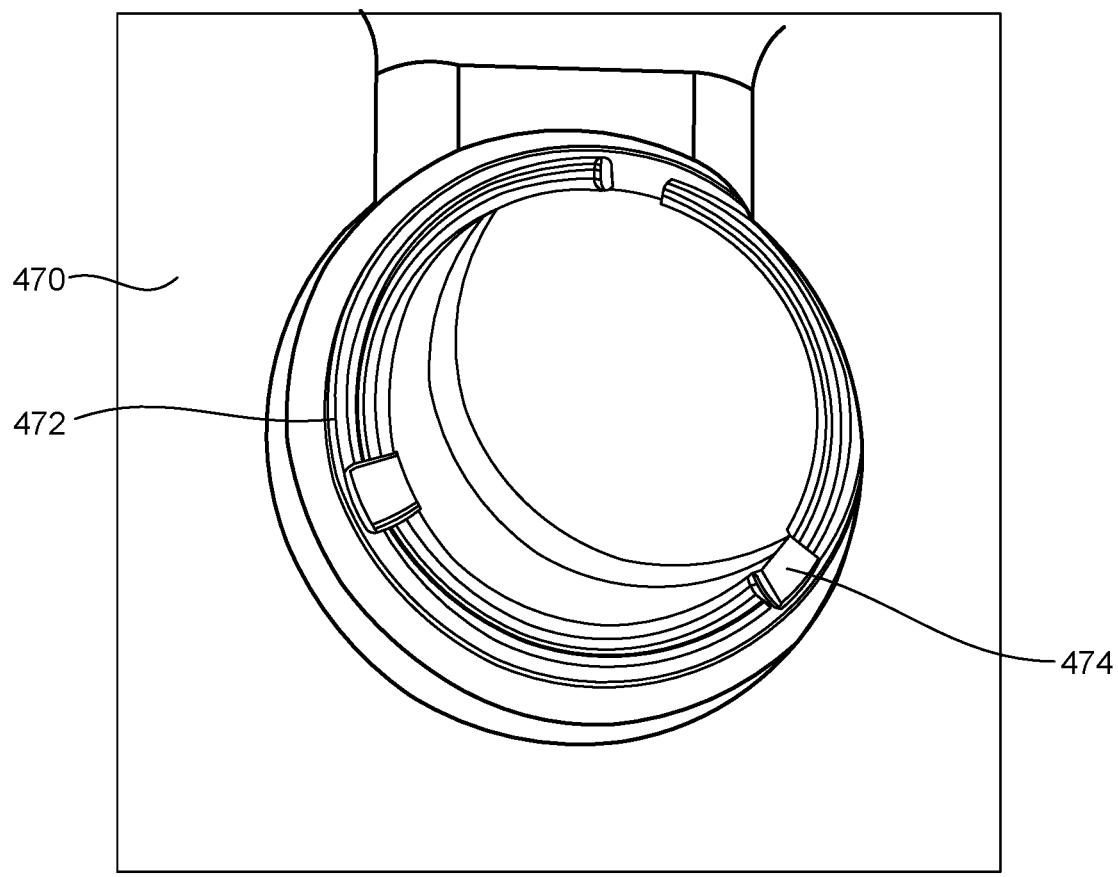

FIGS. 6-7 illustrate a pump assembly 306 according to an aspect. In the illustrated embodiment, as best illustrated in FIG. 7, the slots or grooves 372 defined by the valve body 370 are linear or extend linearly.

FIGS. 8-11 illustrate a pump assembly 406 according to an aspect. In the illustrated embodiment, the movable valve element 440 includes a surface 442 that is configured to engage or contact the sealing surface 472 of the valve body 470.

The surface 442 includes a projection 445. In the illustrated embodiment, the projection 445 forms a ring. In other embodiments, the projection 445 does not form a ring and the surface 442 may include a plurality of projections. The sealing surface 472 includes an indent or a receiving portion 475 that is configured to engage or receive the projection 445. In the illustrated embodiment, the engagement of the projection 445 and the receiving portion 475 facilitates the sealing of the valve components and allows the fluid to reach the slots or grooves 474 in the event of a large amount of pressure on the movable valve element 440.

Figure 12:
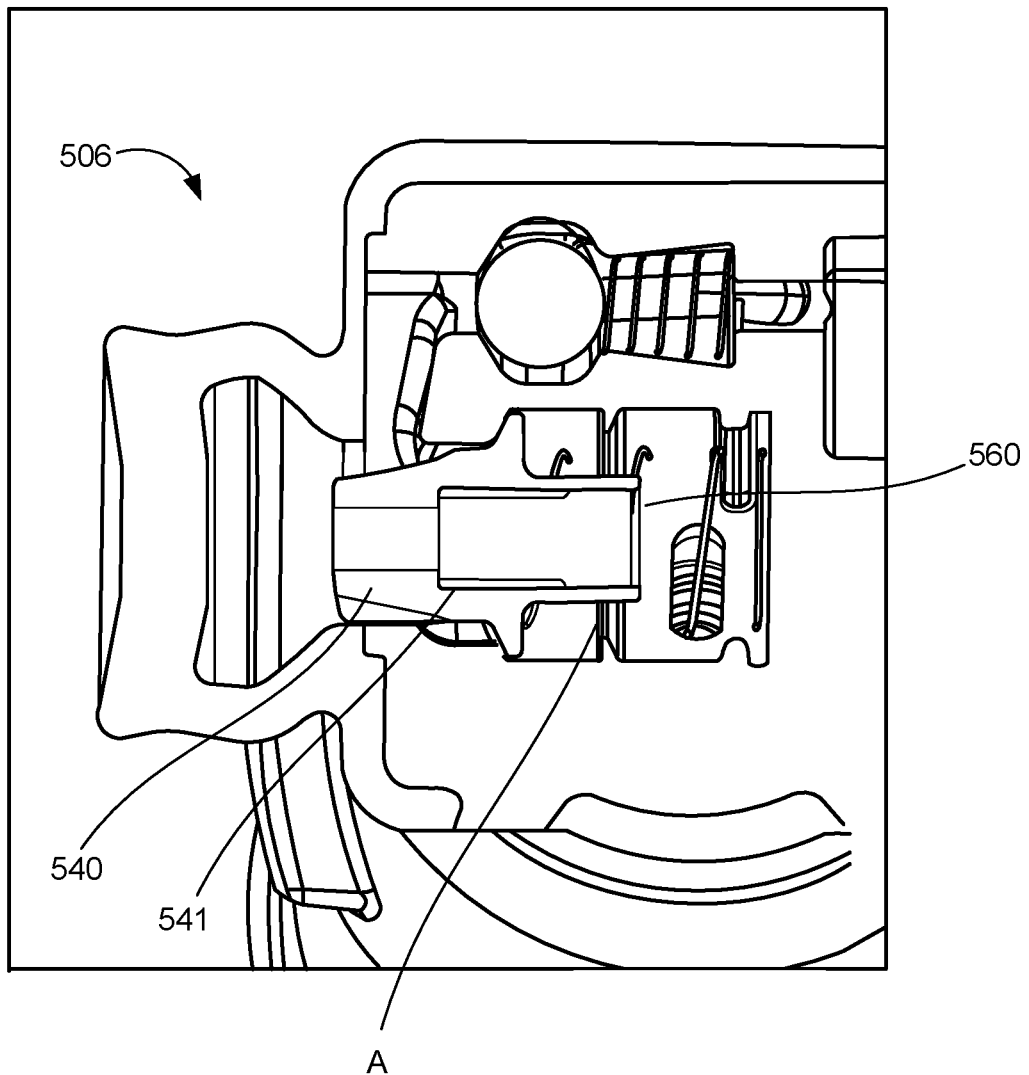
FIG. 12 illustrates a portion of a penile prosthesis according to an aspect.

FIG. 12 illustrates a pump assembly 506 according to an aspect. In the illustrated embodiment, the movable valve element 540 defines a lumen 541. A valve or a secondary valve 560 is disposed within the lumen. The secondary valve 560 is configured to relieve pressure on the movable valve element 540 when there is excess pressure in area A of the pump assembly 506.

Figure 13:
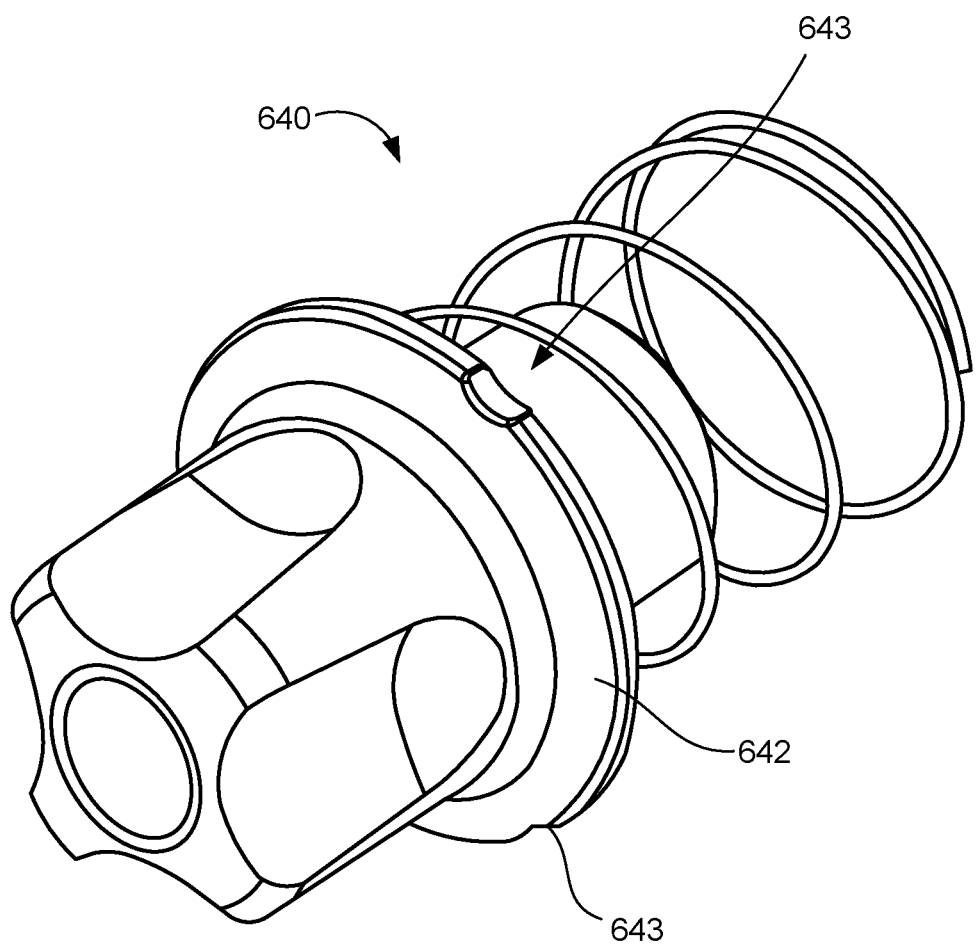
FIGS. 13-15 illustrate a portion of a penile prosthesis according to an aspect.
Figure 14:
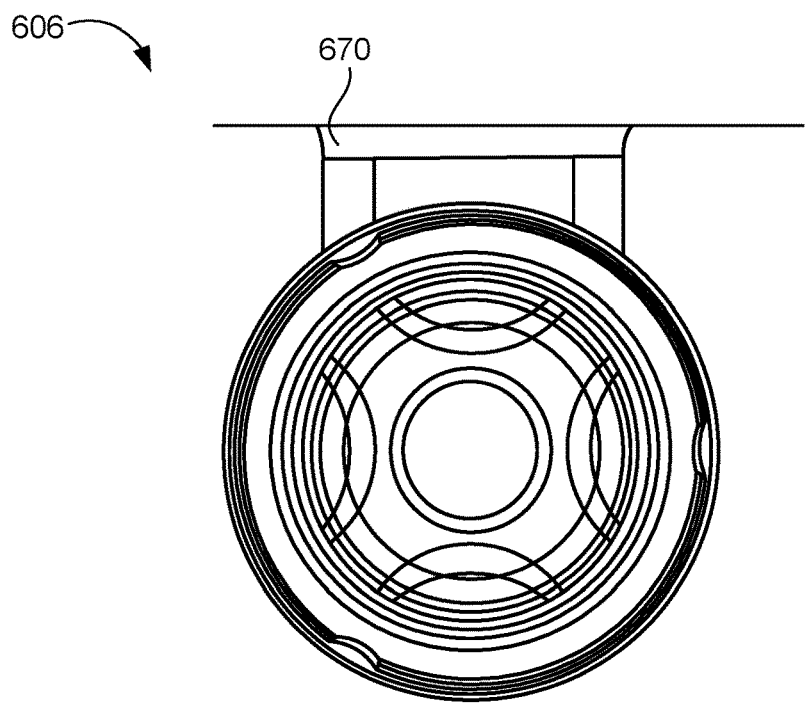
Figure 15:
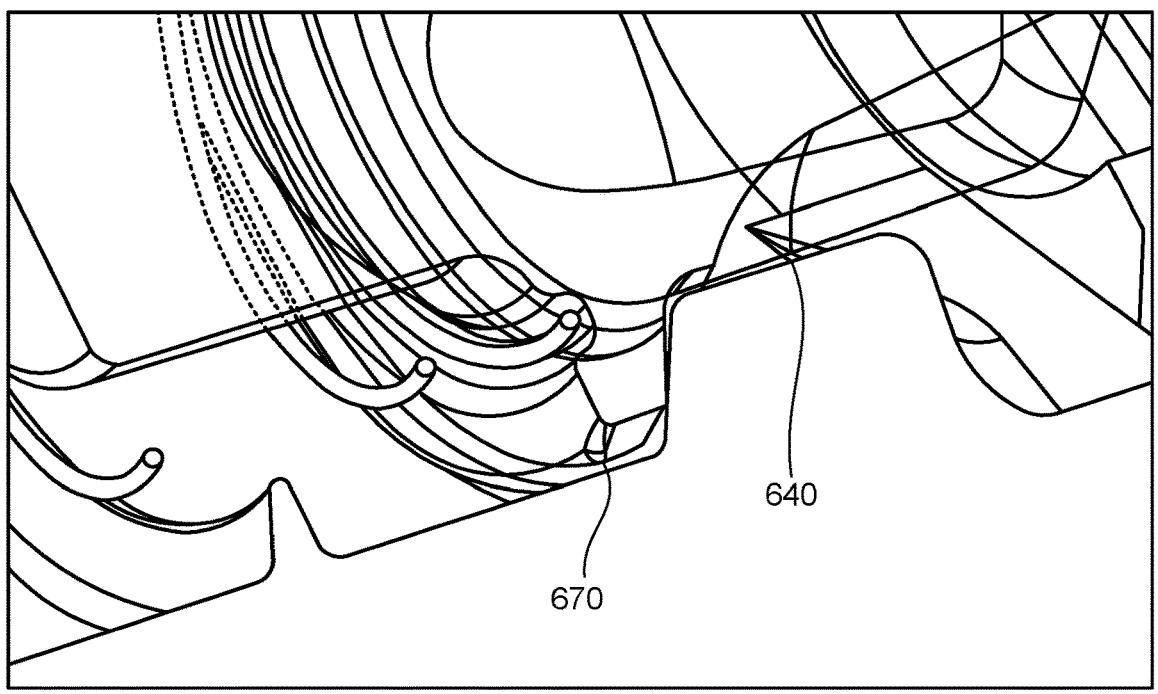

FIGS. 13-15 illustrate a portion of a pump assembly 606 according to an aspect. In the illustrated embodiment, that movable valve element 640 includes a contact surface 642 that is configured to engage a sealing surface 672 of the valve body 670. The contact surface 642 of the includes or defines cutouts or recesses 643. The cutouts or recesses 643 are configured to allow fluid to pass the movable valve element 640 when the movable valve element 640 is exposed to excess pressure.

In the illustrated embodiment, the contact surface 642 includes or defines three cutouts or recesses 643. In other embodiments, the contact surface includes or defines a different number of cutouts or recesses such as one, two, or more than three.

Figure 16:
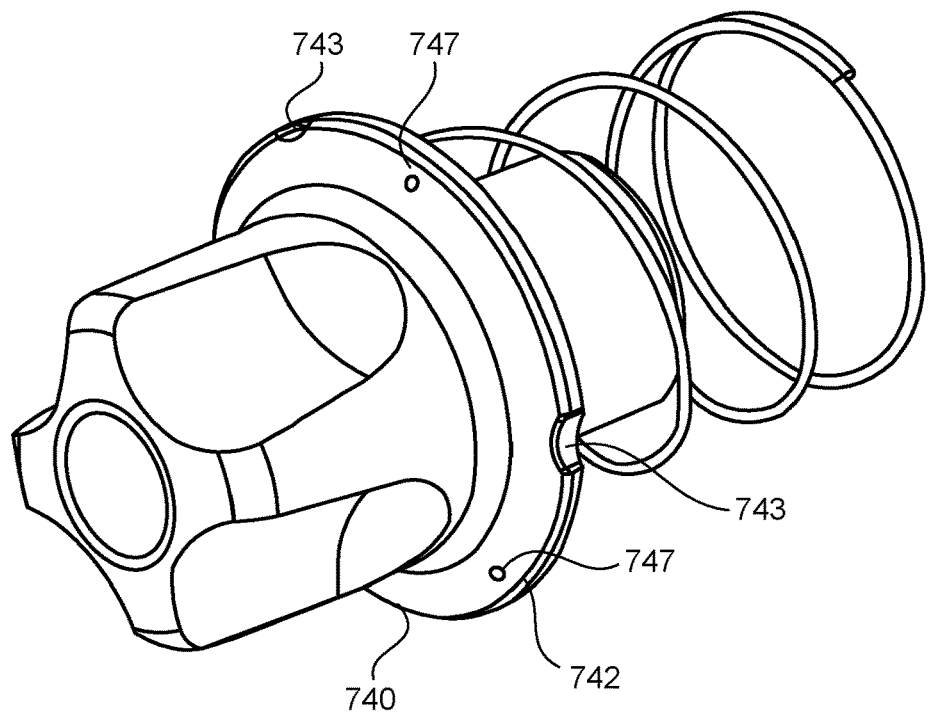
FIGS. 16-17 illustrate a portion of a penile prosthesis according to an aspect.
Figure 17:
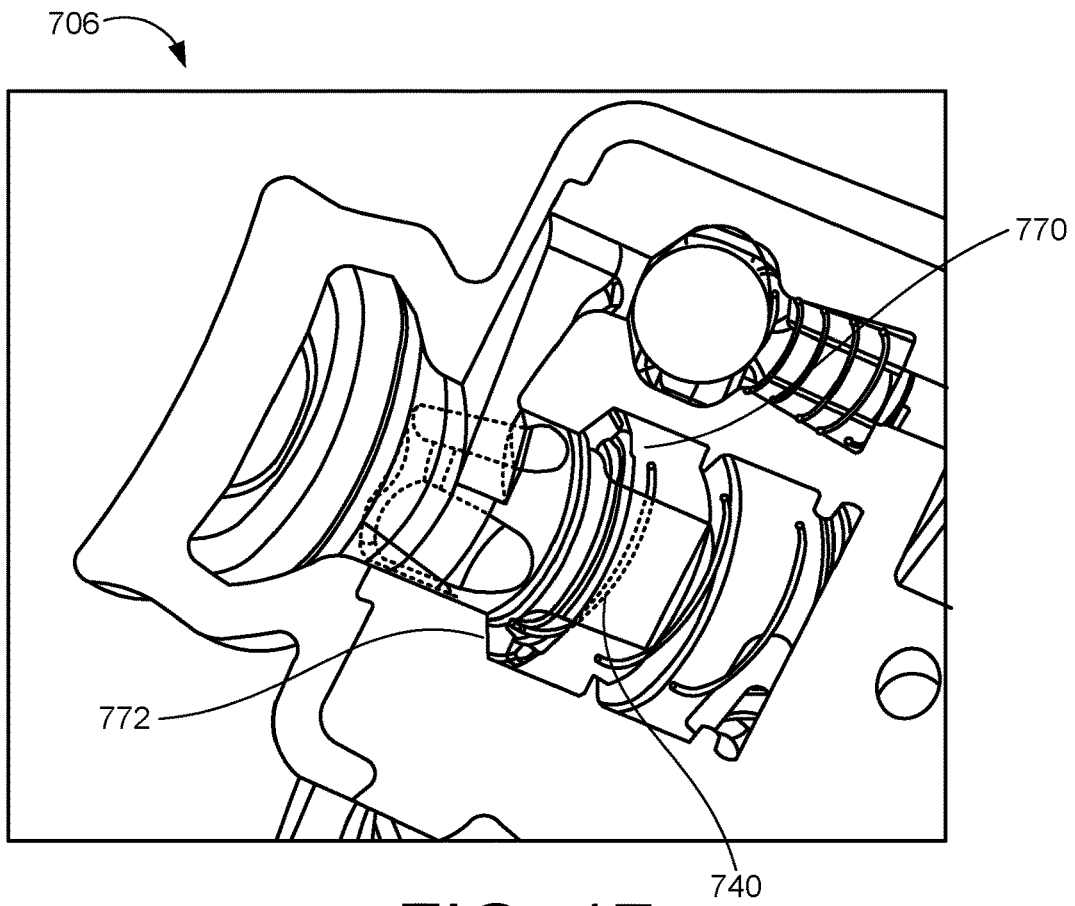

FIGS. 16-17 illustrate a portion of a pump assembly 706 according to an aspect. In the illustrated embodiment, that movable valve element 740 includes a contact surface 742 that is configured to engage a sealing surface 772 of the valve body 770. The contact surface 742 of the includes or defines cutouts or recesses 743. The cutouts or recesses 743 are configured to allow fluid to pass the movable valve element 740 when the movable valve element 740 is exposed to excess pressure.

In the illustrated embodiment, the contact surface 742 includes or defines three cutouts or recesses 743. In other embodiments, the contact surface includes or defines a different number of cutouts or recesses such as one, two, or more than three.

In the illustrated embodiment, the contact surface 742 also includes or defines projections or projection portions 747. In some embodiments, the projection portions 747 are configured to engage the sealing surface 772 of the valve body 770 to facilitate the pressure relief function of the cutouts or recesses 743.

Figure 18:
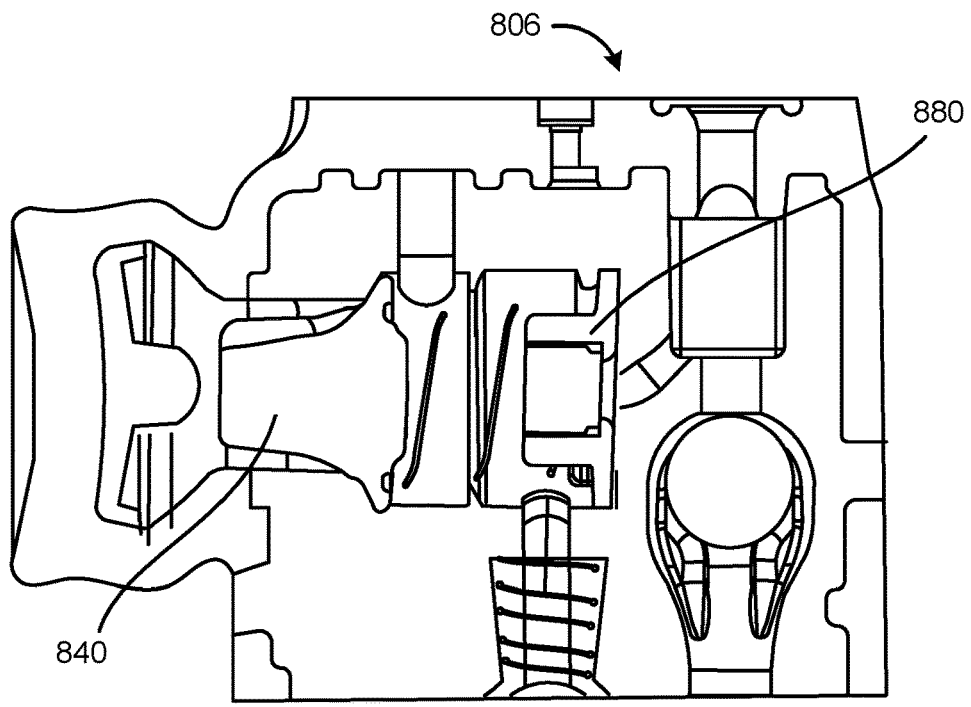
FIG. 18 illustrates a portion of a penile prosthesis according to an aspect.

FIG. 18 illustrates a pump assembly 806 according to an aspect. In the illustrated embodiment, the valve body 870 includes a secondary valve 880. The secondary valve 880 is disposed such that the valve 880 is configured to relieve pressure when there is excess pressure on the movable valve element 840.

Figure 19:
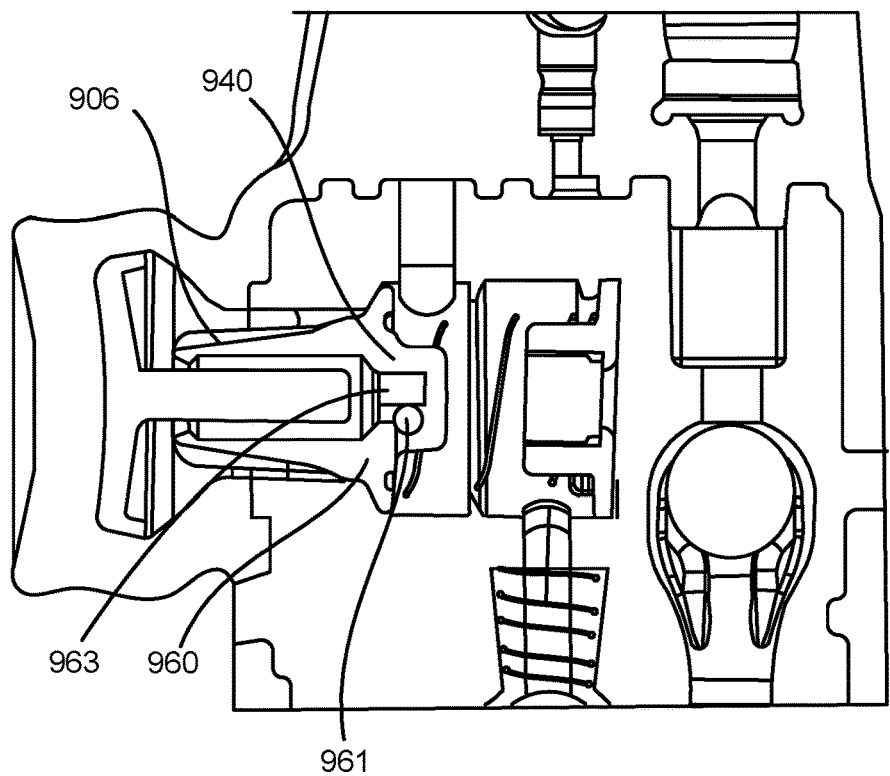
FIG. 19 illustrates a portion of a penile prosthesis according to an aspect.

FIG. 19 illustrates a pump assembly 906 according to an aspect. In the illustrated embodiment, the movable valve element 940 defines a lumen 941. A valve or a secondary valve 960 is disposed within the lumen. The secondary valve 960 is configured to relieve pressure on the movable valve element 940 when there is excess pressure in area B of the pump assembly 906.

In the illustrated embodiment, the secondary valve 960 includes a ball or sphere 961 and a biasing member 963. In other embodiments, the secondary valve includes different components.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An inflatable penile prosthesis, comprising:
a fluid reservoir configured to hold fluid;
an inflatable member; and
a pump assembly configured to transfer the fluid between the fluid reservoir and the inflatable member, the pump assembly including a pump bulb, a valve body, a valve disposed within the valve body, a first fluid port configured to be fluidly coupled to the fluid reservoir, and a second fluid port configured to be fluidly coupled to the inflatable member, the valve being configured to move between an inflation position and a deflation position, wherein the valve body includes a sealing surface configured to engage a sealing surface of the valve to form seal, the valve body includes a slot disposed adjacent the sealing surface, the sealing surface of the valve being disposed fluidically between the slot and the pump bulb, the sealing surface of the valve being disposed between the second fluid port and the slot.

2. The inflatable penile prosthesis of claim 1, wherein the sealing surface is disposed between the slot and the valve.

3. The inflatable penile prosthesis of claim 1, wherein the slot is a first slot, the valve body includes a second slot.

4. The inflatable penile prosthesis of claim 1, wherein the slot is a first slot, the valve body includes a second slot disposed adjacent the sealing surface, the sealing surface being disposed between the second slot and the valve.

5. The inflatable penile prosthesis of claim 1, wherein the valve includes an elongate portion and an engagement portion, the engagement portion having a surface configured to engage the sealing surface of the valve body.

6. The inflatable penile prosthesis of claim 1, wherein the slot is triangular shaped.

7. The inflatable penile prosthesis of claim 1, wherein the slot includes a linear portion.

8. The inflatable penile prosthesis of claim 1, wherein the pump assembly includes a biasing member, the biasing member being configured to bias the valve towards the sealing surface.

9. The inflatable penile prosthesis of claim 1, wherein the pump assembly includes a biasing member, the biasing member being configured to engage the valve and bias the valve towards the sealing surface.

10. The inflatable penile prosthesis of claim 1, wherein the pump assembly includes a spring member.

11. The inflatable penile prosthesis of claim 1, wherein valve includes a surface configured to engage the sealing surface, the surface of the valve including a projection portion.

12. The inflatable penile prosthesis of claim 1, wherein the valve includes a projection portion, the projection portion being configured to engage the sealing surface of the valve body.

13. The inflatable penile prosthesis of claim 1, wherein the valve includes a first member and a second member, the first member being configured to move with respect to the second member.

14. The inflatable penile prosthesis of claim 1, wherein the valve body includes a projection, the valve defines a cavity, the valve cavity being configured to receive at least a portion of the projection of the valve body.

15. The inflatable penile prosthesis of claim 1, wherein the valve defines a groove configured to receive at least a portion of a biasing member.

16. The inflatable penile prosthesis of claim 1, wherein the sealing surface of the valve is disposed between the second fluid port and the slot when the valve is in the inflation position and in the deflation position.

17. An inflatable penile prosthesis, comprising:
a fluid reservoir configured to hold fluid;
an inflatable member;
a pump assembly configured to transfer the fluid between the fluid reservoir and the inflatable member, the pump assembly including a pump bulb, a valve body, a valve disposed within the valve body, a biasing member configured to engage the valve, a first fluid port configured to be fluidly coupled to the fluid reservoir, and a second fluid port configured to be fluidly coupled to the inflatable member, the valve being configured to move between an inflation position and a deflation position, the valve having a sealing surface, the valve body having a sealing surface and defining a slot, the sealing surface of the valve being disposed between the slot and the biasing member, the sealing surface of the valve being disposed between the second fluid port and the slot when the valve is in the inflation position and when the valve is in the deflation position.

18. The inflatable penile prosthesis of claim 17, wherein the valve defines a groove configured to receive a portion of a spring.

19. The inflatable penile prosthesis of claim 17, wherein the valve defines a groove configured to receive a biasing member.

20. An inflatable penile prosthesis, comprising:
a fluid reservoir configured to hold fluid;
an inflatable member; and
a pump assembly configured to transfer the fluid between the fluid reservoir and the inflatable member, the pump assembly including a pump bulb, a valve body, a valve disposed within the valve body, a first fluid port configured to be fluidly coupled to the fluid reservoir, and a second fluid port configured to be fluidly coupled to the inflatable member, the valve being configured to move between an inflation position and a deflation position,
wherein the valve body includes a sealing surface configured to engage the valve to form seal, the valve body includes a first slot disposed adjacent the sealing surface, the valve body includes a second slot disposed adjacent the sealing surface, the sealing surface being disposed between the first slot and the valve, the sealing surface being disposed between the second slot and the valve, the sealing surface of the valve being disposed between the second fluid port and the slot,
wherein the pump assembly includes a biasing member, the biasing member being configured to bias the valve towards the sealing surface.

* * * * *